United States Patent

Powers et al.

[11] Patent Number: 5,916,877
[45] Date of Patent: *Jun. 29, 1999

[54] FLUORESCENT 1-PEPTIDYLAMINOALKANEPHOSPHONATE DERIVATIVES

[75] Inventors: James C. Powers, Atlanta, Ga.; Shin Ono, Toyama, Japan

[73] Assignee: Georgia Tech Research Corporation, Atlanta, Ga.

[ * ] Notice: This patent is subject to a terminal disclaimer.

[21] Appl. No.: 08/911,380

[22] Filed: Aug. 14, 1997

Related U.S. Application Data

[63] Continuation-in-part of application No. 08/324,809, Oct. 18, 1994, Pat. No. 5,681,821.

[51] Int. Cl.⁶ ..................................... A61K 38/05
[52] U.S. Cl. ................................... 514/19; 514/7; 514/18; 530/331; 435/4
[58] Field of Search ................................... 519/18, 19, 7; 530/331; 435/4

[56] References Cited

U.S. PATENT DOCUMENTS 5,106,762   4/1992   Bvedehorst ............................ 436/546

*Primary Examiner*—Cecilia J. Tsang
*Assistant Examiner*—David Lukton
*Attorney, Agent, or Firm*—Deveau, Colton & Marquis

[57] ABSTRACT

Fluorescent 1-peptidylaminoalkanephosphonate derivatives, and their use in detecting and studying the distribution of serine proteases in cells and biological systems.

20 Claims, No Drawings

FLUORESCENT 1-PEPTIDYLAMINOALKANEPHOSPHONATE DERIVATIVES

This is a continuation-in-part of applications Ser. No. 08/324,809 filed on Oct. 18, 1994 now U.S. Pat. No. 8,681,821.

1. FIELD OF THE INVENTION

This invention relates to a novel class of fluorescent peptidyl derivatives of aromatic diesters of 1-aminoalkanephosphonic acid useful for selectively inhibiting elastases, selectively inhibiting chymotrypsin-like enzymes, selectively inhibiting trypsin-like enzymes or for generally inhibiting serine proteases of many classes.

2. DESCRIPTION OF THE RELATED ART

Serine proteases play critical roles in several physiological processes such as digestion, blood coagulation, complement activation, fibrinolysis, viral infection, fertilization, and reproduction. Serine proteases are not only a physiological necessity, but also a potential hazard if they are not controlled. Uncontrolled proteolysis by elastases may cause pancreatitis, emphysema. rheumatoid arthritis, bronchial inflammation and adult respiratory distress syndrome. Human polymorphonuclear leukocyte elastase may also be involved in blistering. Accordingly, potent and specific inhibitors of these proteases tagged with fluorescent molecules can be used to detect, localize, and quantify these enzymes in different types of cells and biological systems. Serine proteases inhibited by these fluorescent compounds can be detected at the single cell level.

Many classes of phosphorus containing compounds have been prepared for use as inhibitors of serine proteases. One useful class reported by Oleksyszyn and Powers are peptidyl derivatives of α-aminoalkylphosphonate diphenyl esters (Irreversible Inhibition of Serine Proteases by Peptide Derivatives of (α-aminoalkyl)phosphonate Diphenyl Esters, Oleksyszyn, J. and Powers, J. C., *Biochemistry*, 1991, 30, 485–493). Other members of the class were described by Bartlett, P. A. and Lamden, L. A., *Bioorg. Chem.*, 1986, 14, 356–377 and Lamden, L. A. and Bartlett, P. A., *Biochem. Biophys. Res. Commun.*, 1983, 112, 1085–1090. These compounds are useful inhibitors for the serine proteases such as elastases, chymotrypsin, chymotrypsin-like enzymes, trypsin, trypsin-like enzymes, blood coagulation enzymes, kallikrein, plasmin, thrombin, and granzymes. Another class of diphenyl peptide phosphonate esters was published by Oleksyszyn et al., 1994 (Novel Amidine-Containing Peptidyl Phosphonates as Irreversible Inhibitors for Blood Coagulation and Related Serine Proteases Oleksyszyn, J., Boduszek, B., Kam, C.-M., and Powers, J. C., *J. Med. Chem.* 1994, 37, 226–231). This class included peptides with C-terminal phosphonate residues related to ornithine, lysine, arginine, or containing a C-terminal diphenyl ester of 1-amino-1-(4-amidinophenyl)methanephosphonate ((4-AmPh)Gly$^P$(OPh)$_2$) or 1-amino-1-(4-amidinophenyl-methyl)methanephosphonate ((4-AmPhe)$^P$(OPh)$_2$). These peptide phosphonates are specific and potent inhibitors of trypsin, thrombin, kallikrein, trypsin-like enzymes, coagulation enzymes, and granzymes. A few other arginine and ornithine analogs and peptidyl phosphonates containing (α-amino-γ-methoxybutyl)phosphonyl or (α-amino-n-hexyl)phosphonyl residues at the P1 site have been reported to be inhibitors of trypsin and thrombin (Fastrez et al., *Tetrahedron Lett.*, 1989, 30, 6861–6864; Cheng et al., *Tetrahedron Lett.*, 1991, 32, 7333–7336; Wang et al., *Tetrahedron Lett.*, 1992, 33, 7667–7670; and Hamilton et al., *Tetrahedron Lett.*, 1993, 34, 2847–2850). None of the diphenyl peptide phosphonate esters mentioned above has fluorescent label attached to it. Tagging these inhibitors with fluorescent labels will render them excellent tools for studying the distribution of serine proteases as well as measuring their quantities in natural killer cells, lymphocyte cells, and all other types of cells and biological systems.

BRIEF SUMMARY OF THE INVENTION

We have found that diphenyl 1-pepidylaminoalkanephosphonate esters tagged with fluorescent groups such as fluorescein or sulforhodamine 101 are potent inhibitors of elastases, chymases, trypsin-like enzymes, granzymes, and other serine proteases. These fluorescent compounds are made by coupling fluorophores to peptidylphosphonates using spacer groups between the peptide and the fluorophore. The spacer groups are inserted in order to prevent unfavorable steric interactions between the fluorophore and the active site of the protease. These compounds can be used to irreversibly label discrete granule-like regions of the natural killer (NK) cells. These fluorescent peptide phosphonates can be used to selectively inhibit serine proteases within whole cells. These fluorescent compounds can also be used to localize serine proteases inside cellular granules. These fluorescent compounds can also be used to selectively or generally inhibit serine proteases either in vitro or in biological systems. The properties of these fluorescent compounds indicate that they will be excellent tools for the study of the distribution of serine proteases in lymphocytes and their role during cytotoxic T-lymphocyte killing. Use of these inhibitors with different peptide sequences with varying specificities and different fluorophores will allow the simultaneous detection of different proteases in cytotoxic lymphocytes as well as in other cells and biological systems.

It is an object of this invention to find a novel group of specific fluorescent inhibitors for elastase, chymotrypsin, trypsin, and other serine proteases of similar substrate specificity and for serine proteases in general. Inhibitors are compounds that can reduce or elimnate the catalytic activity of the enzyme. Trypsin and trypsin-like enzymes normally cleave peptide bonds in proteins and peptides where the amino acid residue on the carbonyl side of the split bond (P1 residue) is Lys, or Arg. Elastase and elastase-like enzymes, on the other hand, cleave peptide bonds where the P1 amino acid is Ala, Val, Ser, Leu and other similar amino acids. Chymotrypsin and chymotrypsin-like enzymes hydrolyze peptide bonds where P1 amino acid is Trp, Tyr, Phe, Met, Leu or other amino acid residues which contain aromatic or large alkyl side chains. All of the above enzymes have extensive secondary specificity and recognize amino acid residues removed from the P1 residue.

It is a further object of this invention to define new fluorescent protease inhibitors, especially inhibitors for chymotrypsin and chymotrypsin-like enzymes, elastases, blood coagulation enzymes, tryptases, trypsin-like enzymes, kallikrein, and granzymes. Such inhibitors could be used to identify and localize new proteolytic enzymes encountered in research. The inhibitors of this invention would be useful for studying the role and the distribution of serine proteases found in cytotoxic T lymphocyte and natural killer cells. These inhibitors are useful for controlling, detecting, and measuring the active serine proteases involved in tumor invasion, blood coagulation and various inflammatory conditions mediated by serine proteases. The inhibitors of this invention would be useful for studying the distribution and role of natural killer and cytotoxic lymphocyte serine proteases.

It is yet another object of this invention to define a novel group of specific inhibitors useful in vitro for inhibiting trypsin, elastase, chymotrypsin and other serine proteases of similar specificity. These inhibitors can be used in research to detect and measure undesired serine proteases found in all cells, tissues, and fluids.

These and other objects are accomplished by the present invention which defines novel fluorescent peptidyl derivatives of aryl diesters of 1-aminoalkanephosphonic acids. These fluorescent phosphonate derivatives are potent inhibitors of serine proteases including chymotrypsin-like enzymes, trypsin-like enzymes, elastase-like enzymes, and other enzymes with other substrate specificities. The fluorescent peptide phosphonates are stable in buffer or plasma, and inhibit the serine proteases to give stable inhibited enzyme derivatives that can easily be detected using confocal microscopy and other ways. The fluorescent peptide phosphonates can be used in both in vitro and in vivo.

DETAILED DESCRIPTION OF THE INVENTION

Fluorescent peptidyl derivatives of aryl diesters of 1-aminoalkanephosphonic acids have been found to be excellent inhibitors of several serine proteases including human leukocyte elastase, porcine pancreatic elastase, bovine chymotrypsin, granzyme A, granzyme K, bovine trypsin, and other serine proteases. The fluorescent diesters of 1-peptidylaminoalkanephosphonic acids are analogs of natural α-amino acids and are designated by the generally accepted three letter abbreviations for the amino acid followed by the superscript P. For example diphenyl N-(N-(5-fluoresceinyl)-5-carbamoylpentanoyl)amino(4-amidinophenyl)methanephosphonate hydrochloride which is related to amidinophenylglycine is abbreviated as Fla-Adp-(4-AmPhGly)$^P$(OPh)$_2$. Fla is 5-fluoresceinylamino and Adp is adipoyl.

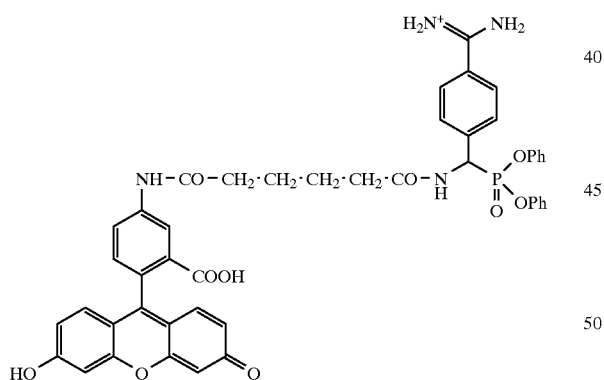

The novel fluorescent peptidyl phosphonate inhibitors and related compounds contain a fluorophore (Fluor) bonded to the peptidyl phosphonate moiety through a spacer group and they have the following general structure:

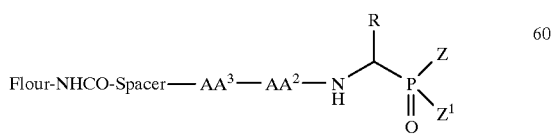

or an acceptable salt, wherein

Fluor is selected from the group consisting of

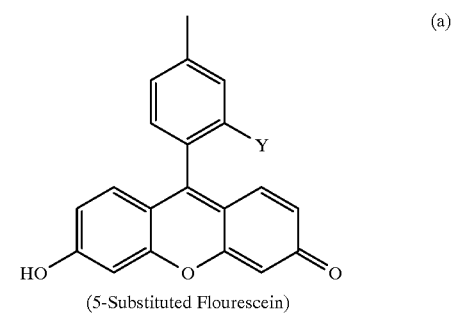

(5-Substituted Flourescein)

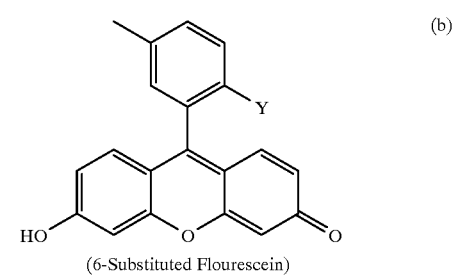

(6-Substituted Flourescein)

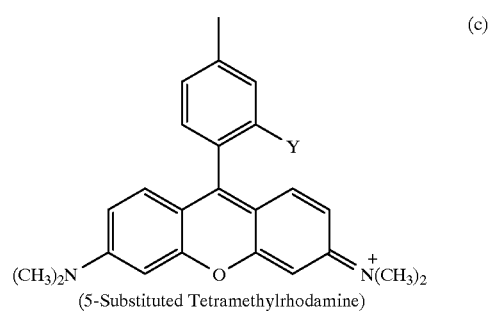

(5-Substituted Tetramethylrhodamine)

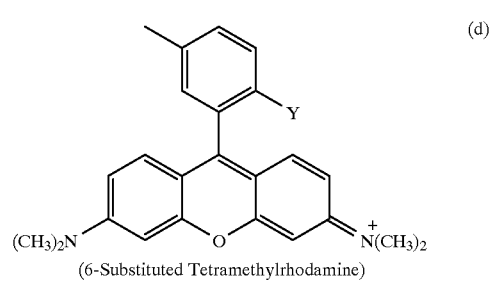

(6-Substituted Tetramethylrhodamine)

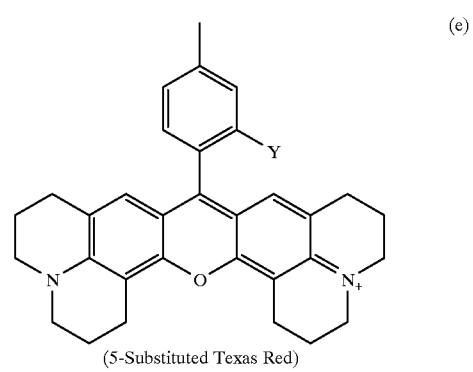

(5-Substituted Texas Red)

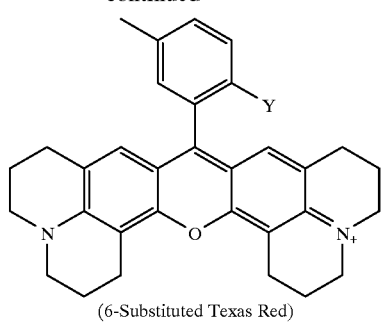

(6-Substituted Texas Red)     (f)

and
(g) an aromatic fluorescent group with an emission maximum of 350 to 700 nm, Y is selected from the group consisting of H, COOH, and $SO_3H$, Spacer is selected from the group consisting of
(a) —$CH_2$—$CH_2$—$CH_2$—$CH_2$—CO—,
(b) —$(CH_2)_n$—CO—,
where n=1 to 12, $AA^3$ and $AA^2$ are the same or different and are selected independently from the group consisting of
(a) a single bond,
(b) a side chain blocked or unblocked amino acid residue with the L or D configuration at the α-carbon selected from the group consisting of alanine, valine, leucine, isoleucine, proline, methionine, methionine sulfoxide, methionine sulfone, phenylalanine, tryptophan, serine, threonine, cysteine, tyrosine, asparagine, glutamine, aspartic acid, glutamic acid, lysine, arginine, histidine, phenylglycine, norleucine, norvaline, alpha-aminobutyric acid, citrulline, hydroxyproline, ornithine, homolysine, and homoarginine, and
(c) glycine, sarcosine, epsilon-aminocaproic acid, and beta-alanine, R is selected from the group consisting of
(a) the side chain of a blocked or unblocked amino acid side chain selected from the group consisting of glycine, alanine, valine, leucine, isoleucine, proline, methionine, methionine sulfoxide, methionine sulfone, phenylalanine, tryptophan, serine, threonine, cysteine, tyrosine, asparagine, glutamine, aspartic acid, glutamic acid, lysine, arginine, histidine, phenylglycine, norleucine, norvaline, alpha-amninobutyric acid, citrulline, hydroxyproline, ornithine, homolysine, and homoarginine, and
(b) phenyl substituted with B, benzyl substituted with B on the phenyl, and $C_{1-6}$ alkyl substituted with B, B is selected from the group consisting of amidino (—C(=NH)$NH_2$), guanidino (—NH—C(=NH)$NH_2$), isothiureido (—S—C(=NH)$NH_2$), and amino, Z and $Z^1$ are the same or different and are selected independently from the group consisting of phenoxy, phenoxy substituted with J, phenoxy disubstituted with J, phenoxy trisubstituted with J, halogen, and $C_{1-6}$ alkoxy, and J is selected from the group consisting of halogen, $C_{1-6}$ alkyl, $C_{1-6}$ perfluoroalkyl, $C_{1-6}$ alkoxy, and CN, Both Z and $Z^1$ can't simultaneosly be $C_{1-6}$ alkoxy.

The fluorophores used in this invention are those well known in the art of fluorescence. Examples of fluorophores include sulforhodamine (Texas Red), tetramethylrhodamine, rhodamine X, and fluorescein as well as their derivatives and tautomeric forms (see structures below). The fluorescent group can also be any fluorophore which can be attached to the spacer and can emit in the range of 350–700 nm.

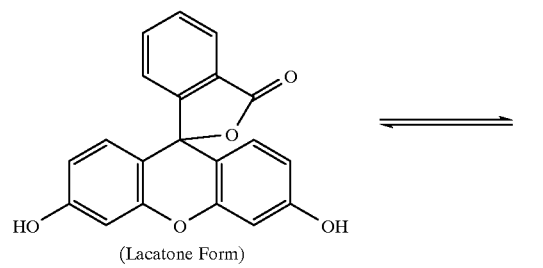

(Lacatone Form)

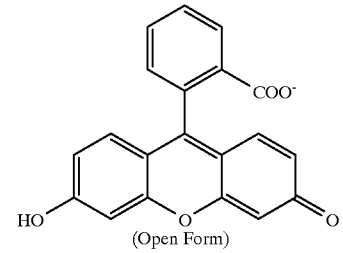

(Open Form)

Flourescein

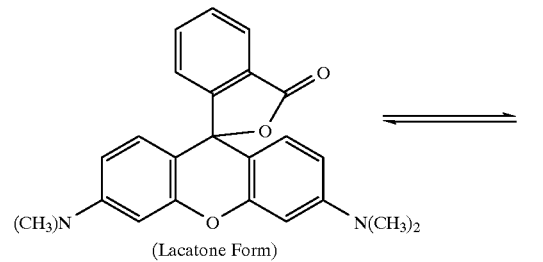

(Lacatone Form)

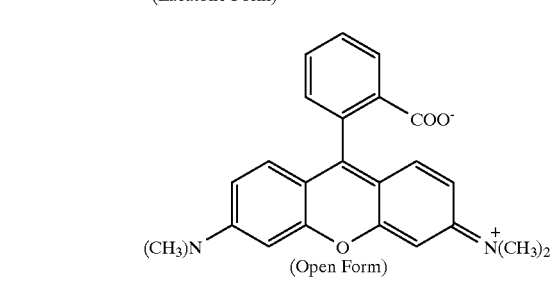

(Open Form)

Tetramethylrhodamine

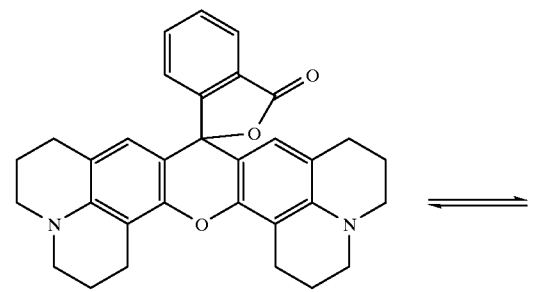

(Lactone Form)

-continued

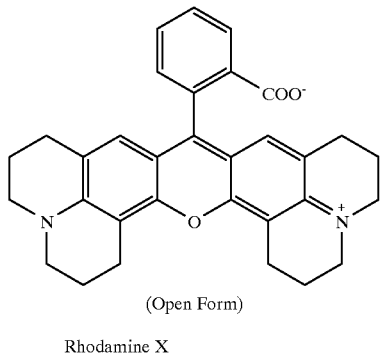

(Open Form)

Rhodamine X

Fluorescent peptidyl derivatives of aryl diesters of 1-aminoalkanephosphonic acids inhibit serine proteases by reaction with the active site serine to form phosphonylated enzymes, which due to similarity of the phosphorus atom to the tetrahedral intermediate formed during peptide hydrolysis, show remarkable stability. The enzyme catalytic apparatus is required to activate the phosphorus atom for nucleophilic substitution and reaction with enzyme. The activation is mainly due to precise interaction with the $S_1$ pocket of various serine proteases. The following figure shows the reaction course of a phosphonate with a serine protease. The phosphonate first binds to the enzyme (below left) and then reacts to form a covalent bond with the active site serine residue (below right). Slow aging can take place with loss of the phenoxy group (below center).

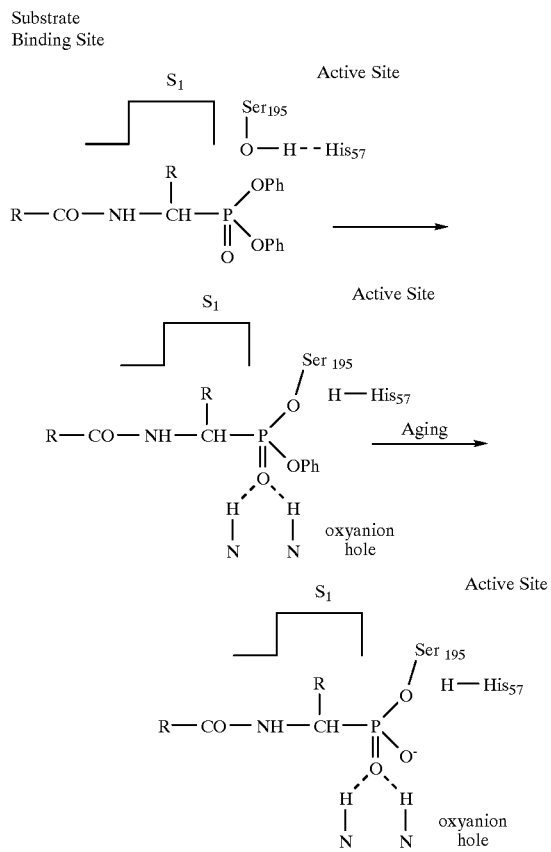

Peptides with a C-terminal phosphonate residue which is an analog of valine (e.g. $Val^P(OPh)_2$) are potent and specific irreversible inhibitors of elastase and elastase-like enzymes. The peptides with C-terminal phosphonate residues related to phenylalanine, other aromatic amino acids or amino acids with long aliphatic side chains are potent and specific inhibitors of chymotrypsin and chymotrypsin-like enzymes. The peptides with C-terminal phosphonate residues related to ornithine, lysine, argiriine or containing a C-terminal diphenyl ester of amino(4-amidinophenyl) methanephosphonate $((4-AmPhGly)^P(OPh)_2)$ or amino(4-amidinophenylmethyl)methanephosphonate $((4-AmPhe)^P(OPh)_2)$ are specific and potent inhibitors of trypsin and trypsin-like enzymes.

Additional specificity as well as increased activation toward reaction with the enzyme can be introduced into the inhibitor molecule by variation of the amino acid sequence in the peptide portion of the structure. In fact there is a good agreement between the sequence of enzyme substrates such as a peptidyl p-nitroanilides or benzylthioesters and the sequence of an effective peptidyl phosphonate inhibitor. The best inhibitors have the sequence of the best peptidyl p-nitroanilide substrate for a particular enzyme. For example, a potent inhibitor for chymotrypsin is Fla-Adp-$Phe^P(OPh)_2$ (see Table 1) which has an amino acid sequence that is analogous to Suc-Phe-Leu-Phe-SBzl, an excellent substrate for these enzymes. With human leukocyte and porcine pancreatic elastases, a good inhibitor (Fla-Adp-Ala-Ala-$Ala^P(OPh)_2$) has an amino acid sequence similar to Suc-Ala-Ala-Ala-NA and Boc-Ala-Ala-Ala-NA, two excellent substrates for porcine pancreatic elastase, and to the chloromethyl ketone, Ac-Ala-Ala-Ala$CH_2$Cl, a good inhibitor of human leukocyte elastase. Clearly it is possible to design good phosphonate inhibitors for serine proteases based on the peptide sequences found in other potent reversible and irreversible inhibitors for those same serine proteases reported in the literature. In this application, we disclose methods of attached fluorescent groups to those potent phosphonate inhibitors.

The following compounds are representatives of the invention:

Diphenyl N-(N-(5-fluoresceinyl)-5-carbamoylpentanoyl) amino(benzyl)methanephosphonate hydrochloride {Fla-Adp-$(Phe)^P(OPh)_2$}.

Diphenyl N-(N-(5-fluoresceinyl)-5-carbamoylpentanoyl) aiino(4-amidinophenyl)methanephosphonate hydrochloride {Fla-Adp-$(4-AmPhGly)^P(OPh)_2$}.

Diphenyl $N^\alpha$-(-(N-(5-Fluoresceinyl)-5-carbamoyl-pentanoyl)lysylamino(4-amidinophenyl)methanephosphonate hydrochloride {Fla-Adp-Lys-$(4-AmPhGly)^P(OPh)_2$}.

Diphenyl $N^\alpha$-(N-(5-Fluoresceinyl)-5-carbamoylpent-anoyl)-ε-tert-butyloxycabonyllysylamino(4-amidinophenyl) methanephosphonate hydrochloride {Fla-Adp-Lys(Boc)-$(4-AmPhGly)^P(OPh)_2$}.

Diphenyl $N^\alpha$-(-(N-(5-Fluoresceinyl)-5-carbamoylpent-anoyl)theonylamino(4-amidinophenyl)methanephosphonate hydrochloride {Fla-Adp-Thr-$(4-ArPhGly)^P(OPh)_2$}.

Enzyme Kinetics

Inactivation rates of serine proteases by fluorescent peptidylphosphonates were measured by the incubation method. In each case the inactivation experiment was preceded by an enzyme assay in which the hydrolysis of peptide ρ-nitroanilide substrates, catalyzed by chymotrypsin, PPE, HLE, and trypsin was measured in 0.1 M Hepes and 0.5 M NaCl (0.01 M CaCl$_2$ for trypsin), pH 7.5 buffer containing 5–10% Me$_2$SO at 25° C. Stock solutions of substrates were prepared in Me$_2$SO (20 mM) and stored at −20° C. Final substrate concentrations were 0.24 mM. Chymotrypsin activity was assayed with Suc-Val-Pro-Phe-NA. PPE was assayed with Suc-Ala-Ala-Ala-NA. HLE was assayed with MeO-Suc-Ala-Ala-Pro-Val-NA and trypsin was assayed with Z-Arg-NA. The initial rates of hydrolysis were measured at 410 nm ($\epsilon_{410}$=8800 M$^{-1}$cm$^{-1}$) on a Beckman 35 spectrophotometer after 25–50 μL of an enzyme stock solution was added to a cuvette containing 2.0 mL of buffer and 25 μL of substrate.

Each inhibition reaction was initiated by adding a 50 μL aliquot of inhibitor (100–5000 μM in Me$_2$SO) to 0.5 mL of a 0.1 M Hepes, 0.5 M NaCl (0.01 M CaCl$_2$ for trypsin), pH 7.5 buffer containing 50 μL of a stock enzyme solution at 25° C. The enzyme stock solutions were 20 μM chymotrypsin, trypsin, and PPE in 1 mM HCl (pH 3), and 0.4–4 μM HLE in 0.25 M NaAc and 1 M NaCl at pH 5.5. All the enzyme stock solutions were stored at −20° C. prior to use. Aliquots (25 μL) were withdrawn at various intervals and the residual enzymatic activity was measured spectrophotometrically as described above. Pseudo first-order inactivation rate constants ($k_{obsd}$) were obtained from plots of ln $v_t/v_o$ vs time and had correlation coefficients greater than 0.98. Each $k_{obsd}$ was calculated from 5–10 activity determinations which extended to 2–3 half lives. Control experiments were carried out in the same way as described above except Me$_2$SO was added in place of the inhibitor solution in Me$_2$SO. The initial rates of substrate hydrolysis did not change during the first 60 minutes of incubation. These initial rates were used as $v_o$ in the calculation of the inhibition rate constants.

Inhibitor Potency

The fluorescent compound containing a Phe$^P$ was evaluated as an inhibitor of chymotrypsin and cathepsin G and was found to be a very specific inhibitor for chymotrypsin ($k_{obsd}$/(I)=147 M$^{-1}$s$^{-1}$ (Table 1).

TABLE 1

Rate Constants for Inhibition of Cathepsin G and Chymotrypsin by a Fluorescein Phosphonate Inhibitor[a]

| Inhibitor | Cat G[c] | ChT[c] |
|---|---|---|
| Fla-Adp-Phe$^P$(OPh)$_2$ | NI | 147 ± 16 |

[a]Conditions were as follows: 0.1M HEPES, 0.5M NaCl, pH = 7.5 buffer at 25° C. for ChT and PPE, and 0.1M HEPES, 0.5M NaCl, 0.01% Brij 35, pH = 7.5 buffer at 25° C. for cathepsin G. Cathepsin G was assayed with 5 mM Suc-Phe-Leu-Phe-sBzl in HEPES buffer containing 4% DMSO. Chymotrypsin was assayed with 5 mM Suc-Phe-Leu-Phe-NA in HEPES buffer containing 7% DMSO. Final enzymeconcentration in the inhibition mixture was 1.2 μM for ChT and 0.04 μM for cathepsin G.
[b]No inhibition after 30 minutes incubation.
[c]$k_{obs}$/[I]M$^{-1}$s$^{-1}$.

The fluorescent compounds containing an AmPhGly$^P$ residue were evaluated as inhibitors of several trypsin-like enzymes and were found to be a very specific and effective inhibitors (Table 2). For example granzyme A was most effectively inhibited by Fla-Adp-Thr-(4-AmPhGly)$^P$(OPh)$_2$ ($k_{obsd}$/(I)=720 M$^{-1}$s$^{-1}$), but this compound didn't inhibit the mast cell tryptase. The mast cell tryptase was inhibited by only one compound, while thrombin was effectively inhibited by three of the four compounds tested.

TABLE 2

Fluorescein Inhibitors for Trypsin-Like Enzymes.

| | $k_{obs}$/[I](M$^{-1}$s$^{-1}$) | | | |
|---|---|---|---|---|
| inhibitor | granzyme A[a] | tryptase[b] | trypsin[a] | thrombin[c] |
| Fla-Adp-(4-AmPhGly)$^P$(OPh)$_2$ | 210 ± 21 | NI[d] | 210 ± 20 | 16 |
| Fla-Adp-Lys-(4-AmPhGly)$^P$(OPh)$_2$ | 110 ± 2 | 0.5 | 80 ± 5 | NI |
| Fla-Adp-Lys(Box)-(4-AmPhGly)$^P$(OPh)$_2$ | 630 ± 7 | NI | 120 ± 7 | 30 |
| Fla-Adp-Thr-(4-AmPhGly)$^P$(OPh)$_2$ | 720 ± 39 | NI | 280 ± 6 | 40 ± 1 |

[a]Inhibition constants were measured in 0.1M Hepes, 0.01M CaCl$_2$, pH 7.5 at 25° C.
[b]Tryptase inhibition constants were measured in 0.1M Hepes, 10% glycerol and 10 mM heparin, pH 7.5 at 25° C.
[c]Thrombin assays were conducted in 0.1M Hepes and 0.5M NaCl at pH 7.5 buffer at 25° C. The inhibition solutions contained approximately 2% DMSO for tryptase, trypsin, and thrombin, and 7.6% DMSO for granzyme A. The tryptase was obtained from Dr. David A. Johnson. The inhibitor concentration ranged from 23 to 100 mM. The substrate used for each enzyme, except tryptase, was Cbz-Arg-SBzl (0.35–36 mM) in the presence of DTNB (0.7–72 mM).Tryptase kinetic constants were measured with Cbz-Lys-SBzl (0.1 mM) as the substrate in the presence of DTNB (0.2 mM).
[d]NI, no inhibition after 70 min of incubation with tryptase, and 25 min with any of the other enzymes.

The specificity of these phosphonate inhibitors is dependent upon the amino acid sequence in the peptide portion of the inhibitor. In each case, the amino acid sequence was chosen based on the specific sequence of a good substrate or inhibitor for the target enzyme. From our earlier work, it is also clear that the specificities of these fluorescent phosphonates compounds are parallel to those of nonfluorescent analogs and are dependent on the sequences of the peptide portions. Thus, previously reported phosphonate inhibitors can be converted into fluorescent inhibitors simply by attaching the Fla-Adp- moiety to the N-terminus of a peptide phosphonate.

Another advantage of the Fla-Adp- phosphonates is their ease of synthesis and stability compared to previously reported FTC-Aca- derivatives. The compounds of the current invention are much easier to synthesize and are more stable. The Fla-Adp-derivatives have an amide bond linking the Fluor and spacer (i.e. Fluor—NH—CO—CH$_2$CH$_2$—), while the earlier reported FTC-Aca- derivative have an urea or thiourea linkage between the Fluor and spacer (i.e. Fluor—NH—CO—NH—CH$_2$— or Fluor—NH—CS—NH—CH$_2$—). Under the conditions required for the generation of the amidino phenylglycine derivative, the urea was less stable than the amide bond and gave lower yields of the desired products. In addition, there are many commercially available dicarboxylic acids which can be used in the synthesis of analogs of the Fla-Adp- unit in the fluorescent phosphonate derivates of the present invention.

Synthesis

The diphenyl 1-aminoalkanephosphonate esters are synthesized from the appropriate aldehyde, benzyl carbamate, and triphenyl phosphite using previously a reported method (Diphenyl 1-Aminoalkanephosphonates, Oleksyszyn, J., Subotkowska, L., and Mastalerz, P., *Synthesis*, 1979, 985–986). For example, H-Phe$^P$(OPh)$_2$, H-Met$^P$(OPh)$_2$, H-Ala$^P$(OPh)$_2$, H-Val$^P$(OPh)$_2$ can be prepared by reaction of phenylacetaldehyde, 3-(methylthio)propionaldehyde, acetaldehyde, 2-methylpropionaldehyde, respectively, with triphenylphosphite, benzyl carbamate, and acetic acid to give the corresponding Cbz-protected amino acid phosphonates (see scheme below) which can be deblocked by treatment with HBr/HOAc or hydrogenolysis. Likewise the chloro derivative, bis(4-chlorophenyl) 1-(N-benyzyloxycarbonylamino)-3-methylthiopropane-phosphonate, Cbz-Met$^P$(4-Cl-C$_6$H$_4$O)$_2$ can be prepared from tris(4-chlorophenyl)phosphite, benzylcarbamate, and 3-methylthiopropionaldehyde in the presence of acetic acid.

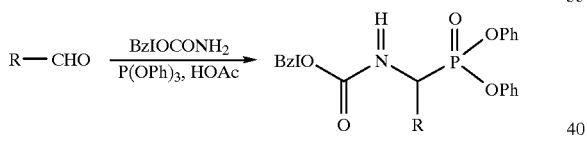

Peptide derivatives can then prepared by sequential coupling of N-blocked amino acids using the DCC coupling method according to the scheme below. For example H-Phe-Leu-Phe$^P$(OPh)$_2$ was prepared by coupling H-Phe$^P$(OPh)$_2$ to Cbz-Leu-OH followed by removal of the Cbz group then coupling to Cbz-Phe-OH and finally removal of the protecting group. H-Ala-Ala-Ala$^P$(OPh)$_2$ and H-Ala-Ala-Met$^P$(OPh)$_2$ were prepared in the same way by coupling H-Ala$^P$(OPh)$_2$ and H-Met$^P$(OPh)$_2$, respectively to Cbz-Ala-OH followed by deblocking, coupling with Cbz-Ala-OH, and deblocking. H-Val-Pro-Val$^P$(OPh)$_2$ was prepared from H-Val$^P$(OPh)$_2$ by coupling with Cbz-Pro-OH, deblocking, coupling with Cbz-Val-OH, and then deblocking.

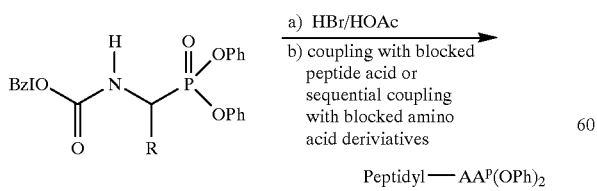

Fluorescein amine is coupled to monomethyl adipoate followed by saponification of the ester group to give Fla-Adp-OH.

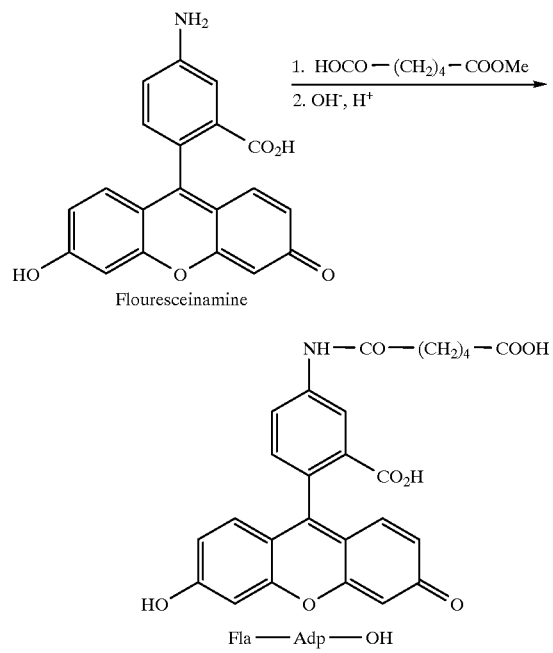

This intermediate can be coupled to the amino acid or peptide phosphonate unit using the DCC coupling method as shown in the scheme below.

Examples of Attachment of the Fla-Adp- Units to Peptide Phosphonates

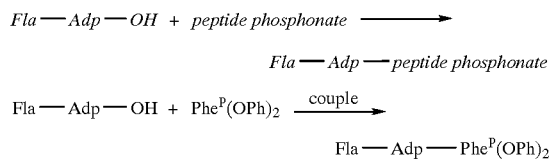

Example of Attachment of the Fluor-Spacer Unit to an Amino Acid Phosphonate

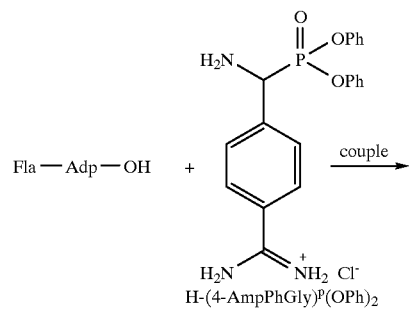

-continued

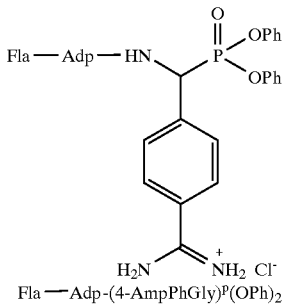

Fla—Adp-(4-AmpPhGly)$^P$(OPh)$_2$

The following examples are given to illustrate the invention and are not intended to limit it in any manner.

General Synthesis Procedures

5-Fluoresceinamine, adipic acid monomethyl ester, and all common reagents and solvents were purchased from Aldrich Chemical Company, Milwaukee, Wis. Porcine pancreatic elastase (PPE) was obtained from United States Biochemical Corp., Cleveland, Ohio. Human leukocyte elastase (HLE) was obtained from Athens Research and Technology, Inc., Athens, Ga. Hepes was obtained from Research Organics, Inc., Cleveland, Ohio. Bovine trypsin was purchased from Sigma Chemical Company, St. Louis, Mo. Preparative thin-layer chromatography was performed with plates precoated with 2 mm of silica gel G.F. and were obtained from EM Separations, Gibbstown, N.J. 08027. NMR spectra were recorded on a Varian GEMINI 300. Elemental analyses were performed by the Atlantic Microlabs, Atlanta, Ga. Diphenyl 1-(N-dipeptidylamino) alkanephosphonate esters were synthesized as previously described (Oleksyszyn and Powers, *Biochemistry*, 1991, 30, 485–493).

EXAMPLE 1

N-Adipoyl-5-aminofluorescein {Fla-Adp-OH}.

Adipic acid monomethylester (0.17 mL, 0.58 mmol) was dissolved in 2 mL of DMF and kept at −10° C. Thionyl chloride (0.10 mL, 1.4 mmol) was added and stirred for 10 min at −10° C. A solution of 5-fluoresceinamine in 2 mL of DMF was added and stirred overnight. The solvent was removed in vacuo. The residue was dissolved in EtOAc. The EtOAc layer was washed with 10% citric acid, water, and sat. NaCl. After drying with Na$_2$SO$_4$ and removal of the solvent, the residue was purified on a silica gel column eluted with CHCl$_3$:MeOH (7:1). Fractions with R$_f$=0.31 were collected and concentrated to give an orange oily residue. Ethyl ether was added to give Fla-Adp-OMe as a yellow solid: yield 29%; one spot on TLC (R$_f$=0.46, CHCl$_3$:MeOH:HOAc, 90:10:1); MS (FAB$^+$) m/e 490 (M+H).

Fla-Adp-OMe (95 mg, 0.19 mmol) was dissolved in 2 mL of MeOH. A solution of 1 N NaOH (0.58 mL) was added and the mixture was stirred at rt overnight. Most of the MeOH was removed under reduced pressure, and the aqueous solution was placed in an ice bath. Diluted HCl were added dropwise with stirring until the mixture was acidic (pH=2–3) and an orange solid precipitated. The orange supension was dissolved in EtOAc and washed with sat. NaCl. After drying with Na$_2$SO$_4$ and removal of the solvent, the residue was triturated with ethyl ether to give Fla-Adp-OH as a yellow solid: yield 91%; one spot on TLC (R$_f$=0.16, CHCl$_3$:MeOH:HOAc, 90:10:1); high-resolution FAB-MS, m/e (M+H) calcd for 476.1345, found 476.1306. Anal. Calcd for C$_{26}$H$_{21}$NO$_8$0.5H$_2$O: C, 64.27; H, 4.58; N, 2.89. Found: C, 64.40; H, 4.94; N, 2.58.

EXAMPLE 2

Diphenyl N-(N-(5-Fluoresceinyl)-5-carbamoylpentanoyl)amino(4-amidinophenyl) methanephosphonate Hydrochloride {Fla-Adp-(4-AmPhGly)$^P$(OPh)$_2$}.

Fla-Adp-OH (38 mg, 79 μmol) and the dihydrochloride of (4-amidinophenyl)aminomethanephosphonate (36 mg, 79 μmol) were dissolved in 2 mL of DMF followed by addition of 1 equiv of TEA. HOBt (16 mg, 1.5 equiv) and EDC.HCl (18 mg, 1.2 equiv) were added and the mixture was stirred at rt overnight. The solvent was removed in vacuo, and the residue was purified on a silica gel column eluted with CHCl$_3$:MeOH:HOAc (40:10:1). Fractions containing the desired product were collected and concentrated under reduced pressure. Ethyl ether was added to give a yellow solid: yield 54%; one spot on TLC (R$_f$=0.20, CHCl$_3$:MeOH:HOAc, 40:10:1); high-resolution FAB-MS, m/e (M+H) calcd for 839.2482, found 839.2525.

EXAMPLE 3

N$^α$-(N-(5-Fluoresceinyl)-5-carbamoylpentanoyl)-ε-tert-butyloxycabonyllysine {Fla-Adp-Lys(Boc)-OH}.

ε-tert-Butyloxycarbonyllysine methyl ester hydrochloride (65 mg, 210 μmol) was dissolved in 3 ml of DMF. After neutralization by 1 equiv of TEA, Fla-Adp-OH (100 mg, 210 μmol) and 1 equiv of EDC.HCl were added and the mixture was stirred at rt overnight. The solvent was removed in vacuo, and the residue was dissolved in EtOAc. The EtOAc layer was washed with 10% citric acid and sat. NaCl. After drying with Na$_2$SO$_4$ and removal of the solvent, ethyl ether was added to give a yellow solid: yield 55%; one spot on TLC (R$_f$=0.33, CHCl$_3$:MeOH:HOAc (90:10:1)); MS (FAB$^+$) m/e 718 (M+H).

Fla-Adp-Lys(Boc)-OMe (50 mg, 70 μmol) was dissolved in 2 mL of DMF. A solution of 1 N NaOH (0.35 ml) was added and the mixture was stirred at rt for 6 hours. The solvent was removed in vacuo, and 10% citric acid was added to the residue in an ice bath until the mixture was acidic (pH=2–3). The desired product was extracted with EtOAc and washed with sat. NaCl. After drying with Na$_2$SO$_4$ and removal of the solvent, ethyl ether was added to give a yellow solid: yield 93%; MS (FAB$^+$) m/e 704 (M+H).

EXAMPLE 4

Diphenyl {N-Adipoyl-5-aminofluoresceinyl-L-lysylamino}(4-amidinophenyl)methanephosphonate {Fla-Adp-Lys-(AmPhGly)$^P$(OPh)$_2$}.

Fla-Adp-Lys(Boc)-OH (50 mg, 70 μmol) and (4-AmPhGly)$^P$(OPh)$_2$·2HCl (32 mg, 70 μmol) were dissolved in 3 mL of DMF followed by addition of 1 equiv of TEA. HOBt (14 mg, 1.5 equiv) and EDC.HCl (16 mg, 1.2 equiv) were added and the mixture was stirred at rt overnight. The solvent was removed in vacuo, and the residue was purified on a silica gel column eluted with CHCl$_3$:MeOH:HOAc (40:10:1). Fractions containg the desired product were collected and concentrated under reduced pressure. Ethyl ether was added to give a yellow solid: yield 47%; high-resolution FAB-MS, m/e (M+H) calcd for 1067.3956, found 1067.3929.

Fla-Adp-Lys(Boc)-(4-AmPhGly)$^P$(OPh)$_2$ (30 mg, 27 mmol) was dissolved in 1 mL of TFA. After 30 min treatment at rt, the solvent was removed under reduced pressure. Ethyl ether was added to the residue to give a yellow solid: yield 77%; high-resolution FAB-MS, m/e (M+H) calcd 967.3472, found 967.3408.

EXAMPLE 5

N-Adipoyl-5-aminofluoresceinyl-L-threonine {Fla-Adp-Thr-OH}.

L-Threonine methylester hydrochloride (37 mg, 210 μmol) was dissolved in 3 mL of DMF. After neutralization by 1 equiv of TEA, Fla-Adp-OH (100 mg, 210 μmol) and 1.2 equiv of EDC HCl were added and the mixture was stirred at rt overnight. The solvent was removed in vacuo. The residue was dissolved in EtOAc and washed with 10% citric acid, water, and sat. NaCl. After drying with Na$_2$SO$_4$ and removal of the solvent, ethyl ether was added to give a yellow solid: yield 53%; one spot on TLC (R$_f$=0.16, CHCl$_3$:MeOH:HOAc, 90:10:1); MS (FAB$^+$) m/e 591 (M+H).

Fla-Adp-Thr-OMe (67 mg, 110 μmol) was dissolved in 2 mL of DMF. A solution of 1 N NaOH (0.55 mL) was added and the mixture was stirred at rt for 6 hours. The solvent was removed in vacuo, and 10% citric acid was added to the residue in an ice bath until the mixture was acidic (pH=2–3). The desired product was extracted with EtOAc and washed with sat. NaCl. After drying with Na$_2$SO$_4$ and removal of the solvent, ethyl ether was added to give a yellow solid: yield 83%; MS (FAB$^+$) m/e 577 (M+H).

EXAMPLE 6

Diphenyl {N-adipoyl-5-aminofluoresceinyl-L-threonylamino}(4-amidinophenyl) methanephosphonated hydrochloride {Fla-Adp-Thr-(4-AmPhGly)$^P$(OPh)$_2$.

Fla-Adp-Thr-OH (45 mg, 78 μmol) and (4-AmPhGly)$^2$ (OPh)$_2$·2HCl (35 mg, 78 μmol) were dissolved in 3 mL of DMF followed by addition of 1 equiv of TEA. HOBt (16 mg, 1.5 equiv) and EDC HCl (18 mg, 1.2 equiv) were added and the mixture was stirred at rt overnight. The solvent was removed in vacuo, and the residue was purified on a silica gel column eluted with CHCl$_3$:MeOH:HOAc (35:15:1). Fractions containing the desired product were collected and concentrated under reduced pressure. Ethyl ether was added to give a yellow solid: yield 32 mg; one spot on TLC, R$_f$=0.33, CHCl$_3$:MeOH:HOAc (35:15:1); high-resolution FAB-MS, m/e (M+H) calcd for 940.2959, found 940.2984.

What is claimed is:

1. A compound of the formula:

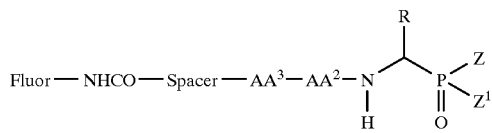

or an acceptable salt, wherein

Fluor is selected from the group consisting of (a)

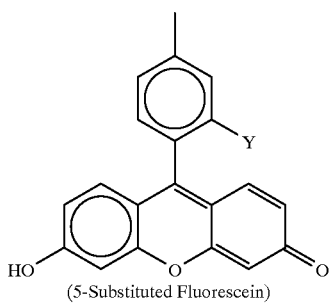

(5-Substituted Fluorescein)

(b)

(6-Substituted Fluorescein)

(c)

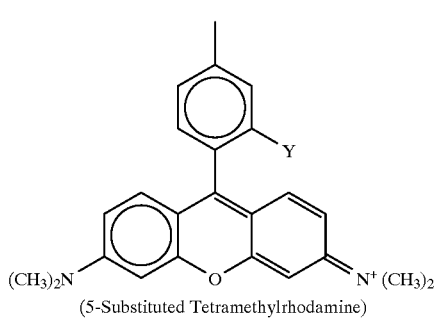

(5-Substituted Tetramethylrhodamine)

(d)

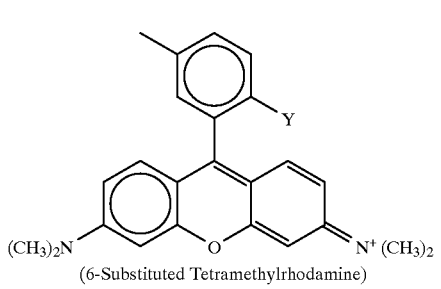

(6-Substituted Tetramethylrhodamine)

-continued

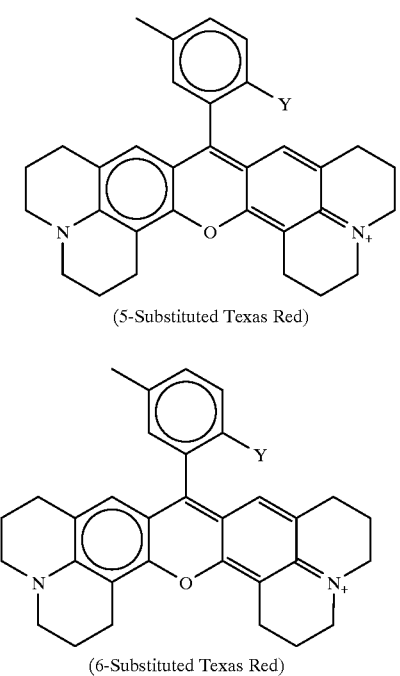

(5-Substituted Texas Red)

(6-Substituted Texas Red)

and (g) an aromatic fluorescent group with an emission maximum of 350 to 700 nm, Y is selected from the group consisting of H, COOH, and $SO_3H$, Spacer is selected form the group consisting of
(a) —$CH_2CH_2$—$CH_2$—$CH_2$—CO—,
(b) —$(CH_2)_n$—CO—,
where n=1 to 12, $AA^3$ and $AA^2$ are the same or different and are selected independently from the group consisting of
(a) a single bond,
(b) an amino acid residue selected from the group consisting of alanine, valine, leucine, isoleucine, proline, methionine, methionine sulfoxide, methionine sulfone, phenylalanine, tryptophan, serine, threonine, cysteine, tyrosine, asparagine, glutamine, aspartic acid, glutamic acid, lysine, arginine, histidine, phenylglycine, norleucine, norvaline, alpha-aminobutyric acid, citrulline, hydroxyproline, ornithine, homolysine, and homoarginine; wherein said amino acid residue is of the D- or L-configuration, and wherein the side chain of said amino acid is optionally blocked, and
(c) glycine, sarcosine, epsilon-aminocaproic acid, and beta-alanine;

R is selected from the from the group consisting of
(a) the side chain of a blocked or unblocked amino acid side chain selected from the group consisting of glycine, alanine, valine, leucine, isoleucine, proline, methionine, methionine sulfoxide, methionine sulfone, phenylalanine, tryptophan, serine, threonine, cysteine, tyrosine, asparagine, glutamine, aspartic acid, glutamic acid, lysine, arginine, histidine, phenylglycine, norleucine, norvaline, alpha-aminobutyric acid, citrulline, hydroxyproline, ornithine, homolysine, and homoarginine, and (b) phenyl substituted with B, benzyl substituted with B on the phenyl, and $C_{1-6}$ alkyl substituted with B, B is selected from the group consisting of amidino (—C(=NH)$NH_2$), guanidino (—NH—C(=NH)$NH_2$), isothiureido (—S—C(=NH)$NH_2$), and amino;

Z and $Z^1$ are the same or different and are selected independently from the group consisting of phenoxy, phenoxy substituted with J, phenoxy disubstituted with J, phenoxy trisubstituted with J, halogen, and $C_{1-6}$alkoxy, and J is selected from the group consisting of halogen, $C_{1-6}$ alkyl, $C_{1-6}$ perfluoroalkyl, $C_{1-6}$alkoxy, and CN;

with the proviso that Z and $Z^1$ cannot simultaneously be $C_{1-6}$ alkoxy.

2. A compound according to claim 1 wherein

Fluor is the structure

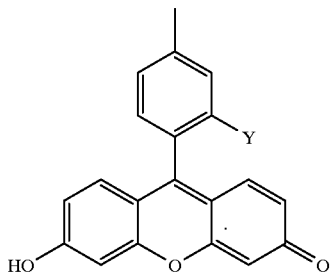

3. A compound according to claim 2 wherein

Y is COOH,

Spacer is —$CH_2$—$CH_2$—$CH_2$—$CH_2$—CO—, $AA^3$ and $AA^2$ are the same or different and are selected independently from the group consisting of
(a) a single bond,
(b) a blocked or unblocked amino acid residue with the L or D configuration at the α-carbon selected from the group consisting of alanine, valine, leucine, isoleucine, lysine, threonine, methionine, phenylalanine, and proline, R is selected from the group consisting of
(a) the side chain of a blocked or unblocked amino acid residue selected from the group consisting of alanine, valine, leucine, isoleucine, methionine, phenylalanine, aspartic acid, lysine, arginine, and phenylglycine,
(b) a phenyl group substituted with B, B is amidino, and Z and $Z^1$ are the same or different and are selected independently from the group consisting of phenoxy or phenoxy substituted with a halogen.

4. A compound according to claim 1 wherein

Fluor is the structure

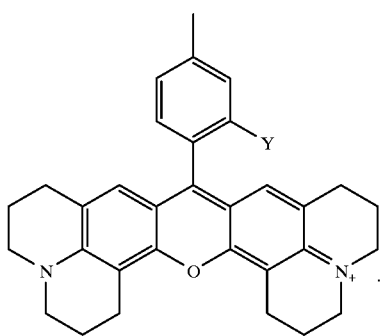

5. A compound according to claim 4 wherein
Y is SO₃H,
Spacer is —CH₂—CH₂—CH₂—CH₂—CO—, AA³ and AA² are the same or different and are selected independently from the group consisting of
  (a) a single bond,
  (b) a blocked or unblocked amino acid residue with the L or D configuration at the α-carbon selected from the group consisting of alanine, valine, leucine, isoleucine, lysine, threonine, methionine, phenylalanine, and proline,
R is selected from the group consisting of
  (a) the side chain of a blocked or unblocked amino acid side chain selected from the group consisting of alanine, valine, leucine, isoleucine, metlionine, phenylalanine, aspartic acid, lysine, arginine, and phenylglycine,
  (b) a phenyl group substituted with B,
  B is amidino, and
Z and Z¹ are the same or different and are selected independently from the group consisting of phenoxy or phenoxy substituted with a halogen.

6. A compound or an acceptable salt of the compound selected from the group of structures consisting of

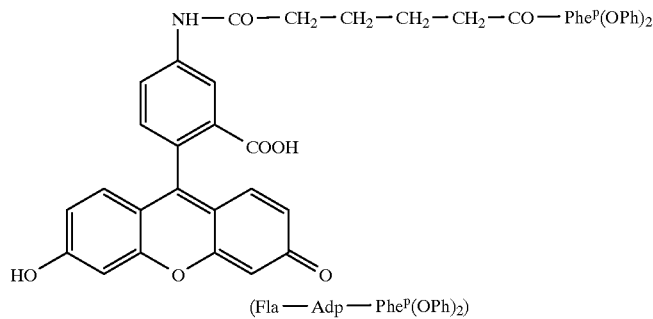

(Fla—Adp—Phe$^p$(OPh)₂)           (a)

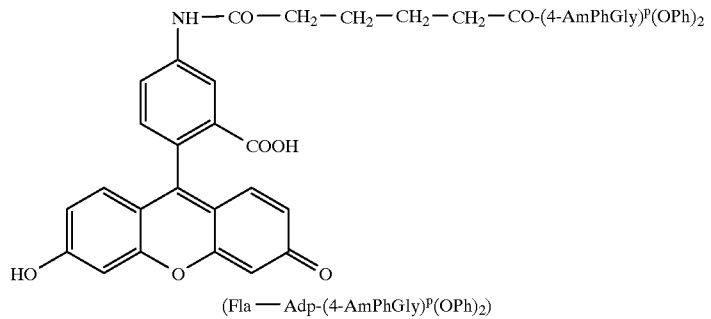

(Fla—Adp-(4-AmPhGly)$^p$(OPh)₂)    (b)

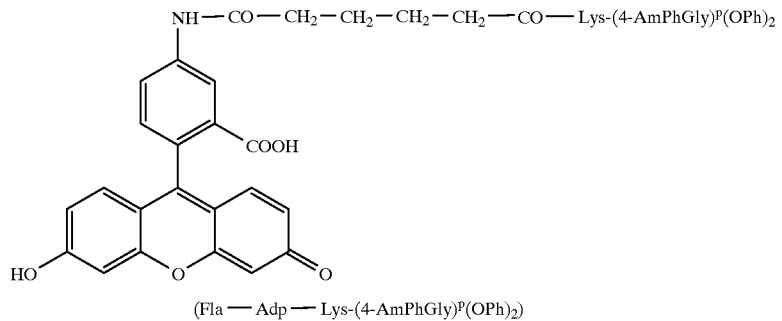

(Fla—Adp—Lys-(4-AmPhGly)$^p$(OPh)₂)  (c)

-continued

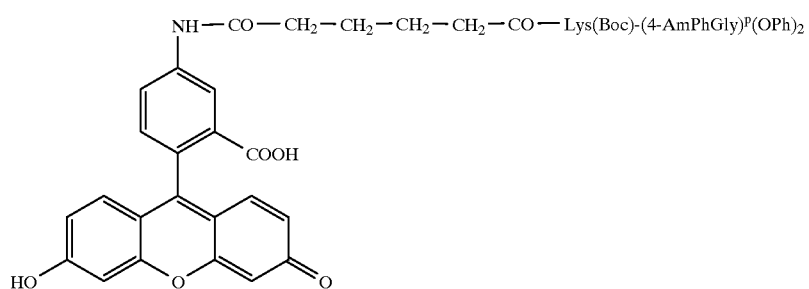

(Fla—Adp—Lys(Boc)-(4-AmPhGly)$^P$(OPh)$_2$).

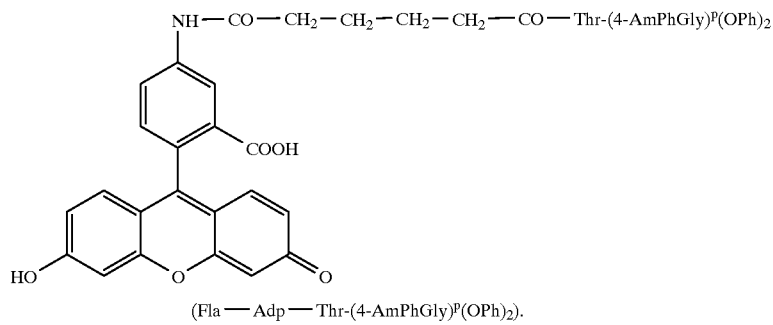

(Fla—Adp—Thr-(4-AmPhGly)$^P$(OPh)$_2$).

7. A compound according to claim 1 wherein AA$^3$ is a sidechain unblocked amino acid residue with the L configuration at the α-carbon.

8. A compound according to claim 1 wherein AA$^3$ is a sidechain unblocked amino acid residue with the D configuration at the α-carbon.

9. A compound according to claim 1 wherein AA$^3$ is a sidechain blocked amino acid residue with the L configuration at the α-carbon.

10. A compound according to claim 1 wherein AA$^3$ is a sidechain blocked amino acid residue with the D configuration at the α-carbon.

11. A compound according to claim 1 wherein AA$^2$ is a sidechain unblocked amino acid residue with the L configuration at the α-carbon.

12. A compound according to claim 1 wherein AA$^2$ is a sidechain unblocked amino acid residue with the D configuration at the α-carbon.

13. A compound according to claim 1 wherein AA$^2$ is a sidechain blocked amino acid residue with the L configuration at the α-carbon.

14. A compound according to claim 1 wherein AA$^2$ is a sidechain blocked amino acid residue with the D configuration at the α-carbon.

15. A compound according to claim 1 wherein AA$^3$ and AA$^2$ are the same.

16. A compound according to claim 1 wherein AA$^3$ and AA$^2$ are different.

17. A compound according to claim 1 wherein Z and Z$^1$ are the same.

18. A compound according to claim 1 wherein Z and Z$^1$ are different.

19. A method for detecting the presence of a serine protease in cells, plasma, and other biological media, comprising contacting the serine protease with a compound according to claim 1.

20. A method for inhibiting a serine protease that is present in cells, plasma, or other biological media, comprising contacting the serine protease with a compound according to claim 1.

* * * * *